(12) United States Patent
Kim et al.

(10) Patent No.: US 10,871,496 B2
(45) Date of Patent: *Dec. 22, 2020

(54) COMPOSITE COMPOUND COMPRISING UPCONVERTING NANOPARTICLE AND SPECIFIC RECEPTOR

(71) Applicant: GWANGJU INSTITUTE OF SCIENCE AND TECHNOLOGY, Gwangju (KR)

(72) Inventors: Min-Gon Kim, Gwangju (KR); Hyo-Young Mun, Gwangju (KR); Eun-Jung Jo, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 897 days.

This patent is subject to a terminal disclaimer.

(21) Appl. No.: 14/979,549

(22) Filed: Dec. 28, 2015

(65) Prior Publication Data

US 2016/0209429 A1 Jul. 21, 2016

(30) Foreign Application Priority Data

Jan. 21, 2015 (KR) .................... 10-2015-0009966

(51) Int. Cl.
| | | |
|---|---|---|
| *G01N 21/359* | (2014.01) | |
| *G01N 33/53* | (2006.01) | |
| *G01N 33/72* | (2006.01) | |
| *C07K 16/18* | (2006.01) | |
| *G01N 33/58* | (2006.01) | |

(52) U.S. Cl.
CPC .......... *G01N 33/723* (2013.01); *C07K 16/18* (2013.01); *G01N 33/587* (2013.01); *G01N 2800/042* (2013.01)

(58) Field of Classification Search
CPC .......................... G01N 21/359; G01N 33/53
See application file for complete search history.

(56) References Cited

U.S. PATENT DOCUMENTS

| | | | | |
|---|---|---|---|---|
| 5,470,759 A | * | 11/1995 | Sugiyama | C07K 16/18 435/14 |
| 9,630,172 B2 | * | 4/2017 | Kim | B01J 21/06 |
| 9,995,741 B2 | * | 6/2018 | Kim | G01N 33/542 |
| 2011/0021970 A1 | * | 1/2011 | Vo-Dinh | A61K 49/0039 604/20 |
| 2013/0183243 A1 | * | 7/2013 | LaBelle | G01N 33/5438 424/9.1 |

OTHER PUBLICATIONS

Thermo-Fisher (https://www.thermofisher.com/us/en/home/life-science/protein-biology/protein-biology-learning-center/protein-biology-resource-library/pierce-protein-methods/carbodiimide-crosslinker-chemistry.html, print retrieved Sep. 26, 2018) (Year: 2018).*

(Continued)

*Primary Examiner* — Tracy Vivlemore
*Assistant Examiner* — Nam P Nguyen
(74) *Attorney, Agent, or Firm* — Novick, Kim & Lee, PLLC; Jae Youn Kim; Jihun Kim

(57) ABSTRACT

Disclosed is a platform detecting glycated hemoglobin as an indicator for diabetes in the blood based on upconverting nanoparticles excited by near-infrared light and luminescence resonance energy transfer.

9 Claims, 9 Drawing Sheets

(56) References Cited

OTHER PUBLICATIONS

Wang et al. (Angew. Chem. Int. Ed., vol. 44, 6054-6057, published 2005) (Year: 2005).*
Wu et al. (Biosensors and Bioelectronic, vol. 30, pp. 35-42, published Aug. 25, 2011) (Year: 2011).*
[Supportive Materials for Exception to Loss of Novelty] Homogeneous Immunosensor for Glycated Detection Based on Luminescence Resonance Energy Transfer Using the Upconversion Nanoparticles, p. 4, on Oct. 23, 2014.

* cited by examiner (Plan view of portable equipment for detecting HbA1c)

(Stereoscopic view of portable equipment for detecting HbA1c)

COMPOSITE COMPOUND COMPRISING UPCONVERTING NANOPARTICLE AND SPECIFIC RECEPTOR

CROSS-REFERENCE TO RELATED APPLICATIONS

This application claims the priority of Korean Patent Application No. KR 10-2015-0009966 filed on Jan. 21, 2015, in the Korean Intellectual Property Office, the disclosure of which is incorporated herein by reference.

BACKGROUND

1. Technical Field

The present invention relates to a complex for diagnosing diabetes including upconverting nanoparticles and a specific receptor and, more particularly, to a complex capable of diagnosing diabetes via glycated hemoglobin (HbA1c) measurement based on luminescence resonance energy transfer (LRET) of upconverting nanoparticles (UCNPs) excited by near-infrared (NIR) light wherein glycated hemoglobin (HbA1c) is an indicator for diabetes in the blood, a diagnostic kit including the same, and a method for preparing the same.

2. Description of the Related Art

Glycated hemoglobin is a form of hemoglobin that is employed to identify the average blood glucose concentration over prolonged periods. In patients with diabetes, higher amounts of glycated hemoglobin indicate poorer control of blood glucose levels. Examples of methods for measuring glycated hemoglobin based on charge differences may include ion exchange chromatography, high performance liquid chromatography (HPLC), electrophoresis, and the like. Examples of methods for measuring glycated hemoglobin based on structural differences may include affinity chromatography and immunoassay.

As a standardized method, high performance liquid chromatography (HPLC) has problems such as technological complexity, high price, and relatively slow reaction. Furthermore, measurement of glycated hemoglobin in a homogeneous state using HPLC is difficult due to matrix effects induced by various by-products in actual samples, and thus requires washing steps and the like in pre-treatment of samples and detection procedures.

The use of biosensors based on fluorescence resonance energy transfer (FRET) has a merit in that it can measure bonds of biomolecules in a homogeneous state. However, this method has disadvantages such as damage to biomolecules by ultraviolet (UV) or visible light used for exciting fluorescent organic materials and quantum dots, and non-specific signals induced by various luminescent by-products in samples.

Recently, it is anticipated that upconverting nanoparticles frequently used in the art can resolve such problems using near-infrared light for excitation. Furthermore, it is also anticipated that the introduction of luminescence resonance energy transfer based on upconverting nanoparticles will allow glycated hemoglobin to be measured in a homogeneous state.

BRIEF SUMMARY

Embodiments of the present invention provide a platform detecting glycated hemoglobin as an indicator for diabetes in the blood based on upconverting nanoparticles excited by near-infrared light and luminescence resonance energy transfer.

One aspect of the present invention relates to a complex including: (i) a specific receptor for glycated hemoglobin; and (ii) upconverting nanoparticles bound to the specific receptor.

Another aspect of the present invention relates to a kit for diagnosing diabetes including a complex according to various embodiments of the present invention.

A further aspect of the present invention relates to a kit for diagnosing diabetes including: (a') surface modified upconverting nanoparticles; and (a") a specific receptor for glycated hemoglobin, wherein the nanoparticles and the receptor are enclosed in separate containers, respectively.

Yet another aspect of the present invention relates to a method for diagnosing diabetes, including: (A) bringing blood taken from the human body into contact with a complex according to various embodiments of the present invention; and (B) exposing the complex brought into contact with blood to near-infrared light irradiation and measuring luminescence intensity.

Yet another aspect of the present invention relates to a method for preparing a complex including an antibody and upconverting nanoparticles bound to the antibody.

In the platform, energy transferred from the upconverting nanoparticles-antibody complex to glycated hemoglobin increases with increasing concentration of glycated hemoglobin. Accordingly, the quenched luminescence signals from the upconverting nanoparticles-antibody complex can be quantitatively measured.

BRIEF DESCRIPTION OF THE DRAWINGS

The above and other aspects, features, and advantages of the present invention will become apparent from the detailed description of the following embodiments in conjunction with the accompanying drawings, in which.

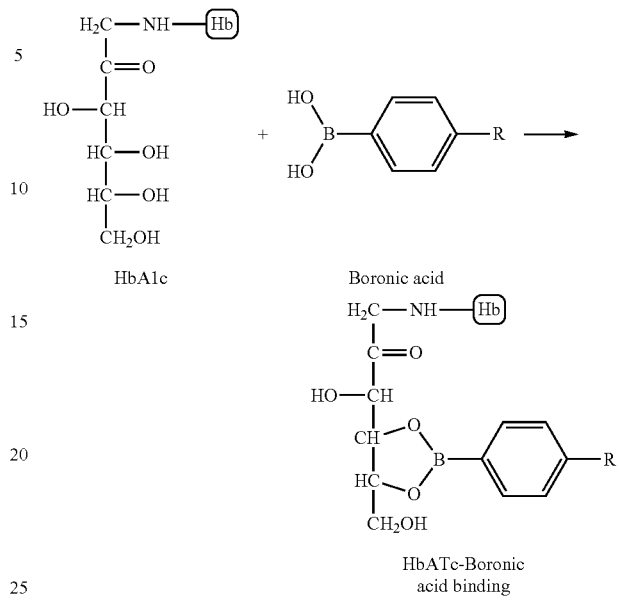

DETAILED DESCRIPTION

Figure 1A:
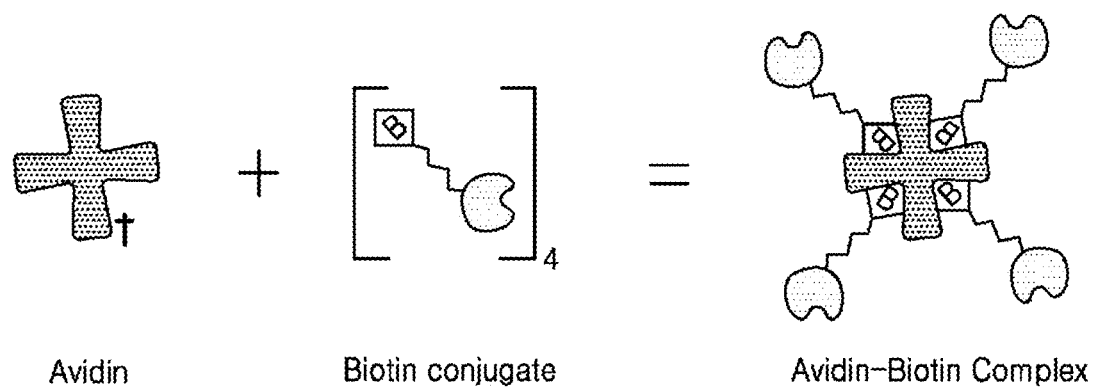
FIG. 1a shows conjugation between avidin and biotin.

One aspect of the present invention relates to a complex including: (i) a specific receptor for glycated hemoglobin; and (ii) upconverting nanoparticles bound to the specific receptor. The complex detects glycated hemoglobin through quenched luminescence signals via luminescence resonance energy transfer in which energy of an excited state of a donor is transferred to an acceptor, wherein the complex including a specific receptor for glycated hemoglobin as an indicator for diabetes in the blood and upconverting nanoparticles are used as the donor and glycated hemoglobin to be detected is used as the acceptor.

In one embodiment, the complex is a complex for detecting glycated hemoglobin or a complex for diagnosing diabetes.

In another embodiment, the specific receptor for glycated hemoglobin is a substance capable of specifically binding to glycated hemoglobin and is at least one selected from the group comprising an antibody, an enzyme, DNA, an aptamer, a peptide nucleic acid (PNA), and a ligand.

The antibody may include at least one selected from the group comprising an anti-HbA1c monoclonal antibody, an anti-HbA1c polyclonal antibody, an anti-glycated albumin monoclonal antibody, and an anti-glycated albumin polyclonal antibody. The enzyme may be a glycolytic enzyme. The DNA may be a glycated hemoglobin bound aptamer. In addition, the ligand may be boronic acid.

In particular, if the antibody is an anti-HbA1c monoclonal antibody, advantageously, the antibody can specifically bind to glycated hemoglobin, which is a macromolecule, as compared to other specific receptors mentioned above, and does not require surface modification and pre-treatment procedures at a terminal of the receptor.

As boronic acid can sufficiently bind to HbA1c, in the case of using boronic acid having an amine group at R group, as shown in the following reaction 1, boronic acid can bind to carboxylated upconverting nanoparticles to form a complex, which is then used in reaction with HbA1c.

In a further embodiment, the upconverting nanoparticles include rare earth elements as a major component. In one implementation, the upconverting nanoparticles include at least one selected from yttrium (Y) and ytterbium (Yb) and at least one selected from erbium (Er), holmium (Ho), and thulium (Tm) as an activator.

In another implementation, the upconverting nanoparticles have a chemical composition represented by Formula 1, 2 or 3:

$NaYF_4: 20\% \ Yb^{3+}, 2\% \ Er^{3+}$ [Formula 1]

$NaYF_4: 20\% \ Yb^{3+}, 2\% \ Ho^{3+}$ [Formula 2]

$NaYF_4: 20\% \ Yb^{3+}, 2\% \ Tm^{3+}$ [Formula 3]

In yet another embodiment, the specific receptor for glycated hemoglobin and the upconverting nanoparticles are bound together by physical bonds or chemical bonds. In one implementation, examples of the physical or chemical bonds may include a covalent bond, an ionic bond, and adsorption.

In particular, covalent bonds may be formed by the following method, wherein a bond between an aldehyde group introduced to surfaces of the upconverting nanoparticles and a specific receptor for glycated hemoglobin may be formed by the following steps: (A) coating upconverting nanoparticles with silica; (B) introducing an amine group to the silica-coated upconverting nanoparticles; (C) converting the amine group to an aldehyde group; and (D) binding the aldehyde group to an amine group of the enzyme, an amine group of the antibody, an amine group of the DNA terminal, or an amine group of the ligand such as aminophenylboronic acid.

Step (A) may be performed by reacting upconverting nanoparticles with tetraethyl orthosilicate, step (B) may be performed using aminopropyl trimethoxysilane, and step (C) may be performed using glutaraldehyde. In addition, step (D) may be performed through forming a Schiff base structure of an amine group of the enzyme, an amine group of the antibody, an amine group of the DNA terminal, and an amine group of the ligand with an aldehyde group of the upconverting nanoparticles, as shown in the following Reaction 2:

[Reaction 2]

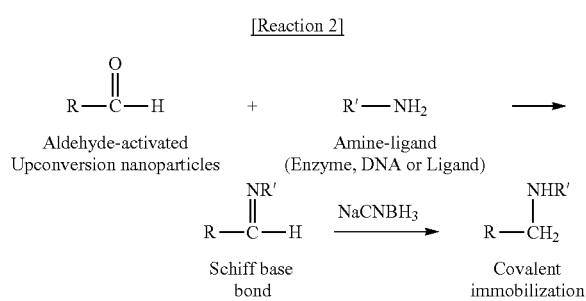

Furthermore, the covalent bond may be formed by a linkage between an epoxy group introduced to the surface of the upconverting nanoparticles and the enzyme, the antibody, the ligand or DNA. Specifically, the covalent bond may be performed by the following steps of: (A) coating upconverting nanoparticles with silica; (B) introducing an epoxy group to the silica-coated upconverting nanoparticles, and (C) binding the epoxy group to an amine group of the enzyme, the antibody or the ligand. In step (C), the epoxy group may be bound to an amine group of the enzyme, an amine group of the antibody, an amine group or a thiol group of the DNA terminal, or an amine group of the ligand.

Step (A) may be performed by reacting upconverting nanoparticles and tetraethyl orthosilicate. Step (B) may be performed using glycidoxypropyltrimethoxysilane. Step (C) may be performed by forming a covalent bond between an amine group of the enzyme, an amine group of the antibody, an amine group or a thiol group of the DNA terminal, or an amine group of the ligand and an epoxy group of the upconverting nanoparticles, as depicted in the following Reactions 3 and 4.

[Reaction 3]

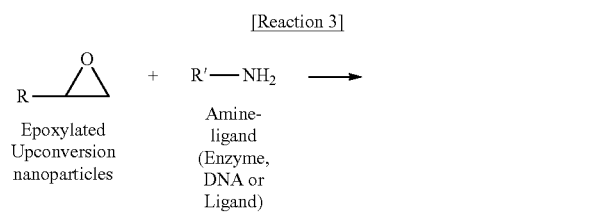

[Reaction 4]

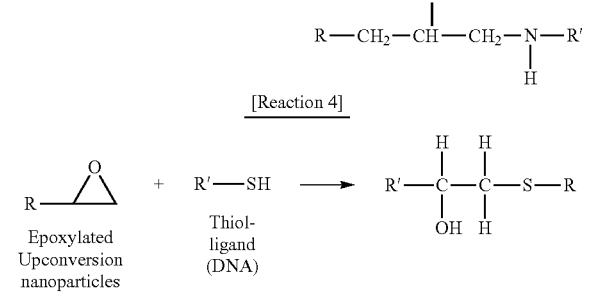

Furthermore, the covalent bond may be formed by reacting a carboxylic group introduced to the surface of the upconverting nanoparticles with the aforementioned enzyme, antibody, ligand or DNA. Detailed description is set forth below.

In yet another embodiment, the specific receptor for glycated hemoglobin is an antibody, and the bond is an amide bond between the carboxylic group introduced to the surface of the upconverting nanoparticles and an amine group of the antibody.

In yet another embodiment, the bond is formed by reacting 1-ethyl-3-(3-dimethylaminopropyl) carbodiimide (EDC) with hydroxysuccinimide (NHS).

Specifically, EDC is added to carboxylated silica-coated upconverting nanoparticles to activate the carboxylic group. Namely, EDC is added in order to activate the reaction to form an unstable intermediate, which is not included in a final complex structure. Then, hydroxysuccinimide (NHS) is added to the intermediate to form an NHS-ester bond. After such EDC/NHS reaction, an antibody is added to form a stable covalent bond via an amide bond with an amine group of the antibody, thereby synthesizing a complex comprised of upconverting nanoparticles-antibody.

[Reaction 5]

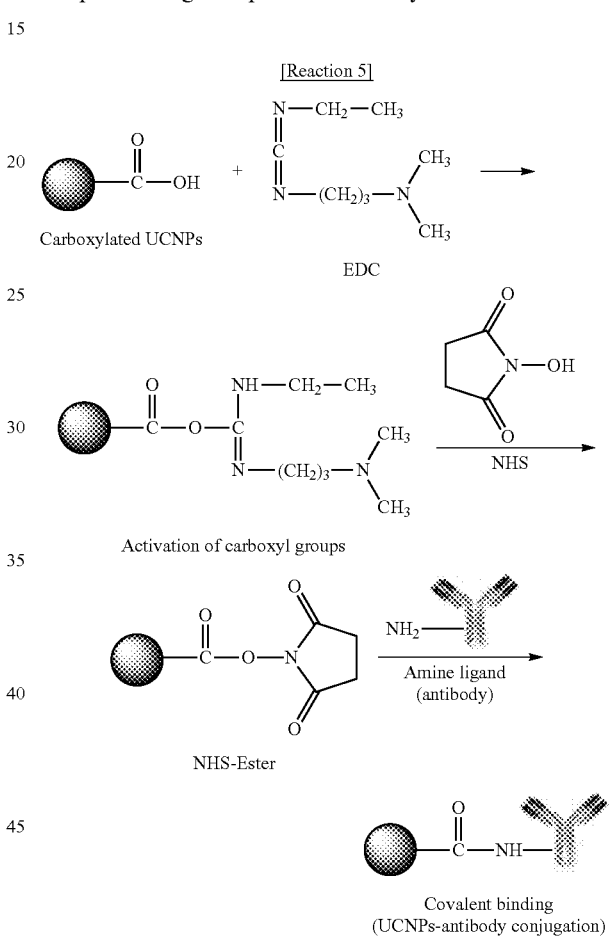

In yet another embodiment, the upconverting nanoparticles are subjected to surface modification by silica coating or polyethylene glycol (PEG) encapsulation.

Silica coating or PEG encapsulation is a method of introducing functional groups to the upconverting nanoparticles in order to form a complex with an antibody. Firstly, in silica coating, an aldehyde group, an epoxy group or a carboxylic group is introduced after silica coating, as depicted above. Details of silica coating are the same as above.

On the other hand, a carboxylic group may be introduced to the upconverting nanoparticles through PEG encapsulation, by which the upconverting nanoparticles are surrounded by PEG-phospholipids to form a micelle structure, thereby obtaining carboxylated upconverting nanoparticles which are dispersible in water.

Specifically, the surface modified upconverting nanoparticles may be obtained by mixing the upconverting nanoparticles with 1,2-dimyristoyl-sn-glycero-3-phosphoethanolamine-N-[methoxy(polyethylene glycol)-2000] (mPEG (2000)) and 1,2-distearoyl-sn-glycero-3-phosphoethanolamine-N-[carboxy(polyethanolglycol)-2000] (DSPE-PEG (2000) Carboxylic Acid) with stirring, followed by evaporating the reaction solvent, and washing the resulting substance.

Besides the covalent bond, the upconverting nanoparticles may be bound to a specific receptor for glycated hemoglobin through a non-covalent bond such as an ionic bond, adsorption, and the like.

Examples of the non-covalent bond may use bond formation between a protein, such as avidin, streptavidin and neutravidin, and a chemical material such as biotin. Such bonds are known to have very high affinity like an antigen-antibody interaction.

It is considered that such bonds result from a combination of the following reasons. Firstly, one reason is that a very complementary shape is formed between a binding pocket of the protein and biotin. Secondly, another reason is that a huge network of hydrogen bonds is formed when biotin is at the binding pocket (binding site). Lastly, a further reason is that since the binding pocket for biotin is hydrophobic, when biotin is at the binding site, Van der Waals force is formed by hydrophobic interaction of biotin.

Accordingly, it is possible to form an upconverting nanoparticles-protein complex by binding an amine of the protein to the upconverting nanoparticles, while it is possible to form an upconverting nanoparticles-antibody complex or a nanoparticles-aptamer complex by binding an antibody to biotin or binding biotin to an aptamer end and then utilizing the aforementioned binding procedure.

In yet another embodiment, the upconverting nanoparticles have an average diameter of 40 nm to 45 nm and the silica coating has an average thickness of 8 nm to 10 nm.

If the size of UCNPs is greater than the upper limit, there is a problem in that the complex can be settled down upon binding various receptors including antibodies to UCNPs, washing and reacting. If the size of UCNPs is less than the lower limit, there is a problem that advantageous effects of the present invention can be insufficiently exhibited.

Furthermore, if the thickness of the silica coating is greater than the upper limit, effective energy transfer is not ensured since the distance between energy donors and acceptors is too far. If the thickness the silica coating is less than the lower limit, there is a possibility that advantageous effects of the present can be insufficiently exhibited.

Another aspect of the present invention relates to a kit for diagnosing diabetes including a complex according to various embodiments of the present invention.

A further aspect of the present invention relates to a kit for diagnosing diabetes including: (a') surface modified upconverting nanoparticles; and (a") a specific receptor for glycated hemoglobin, wherein the particles and the receptor are contained in separate containers, respectively.

The kit further may include (b) a near-infrared light source. The near-infrared light source may include a laser diode emitting light having a wavelength of 980 nm.

In some embodiments, the kit further may include (c) a detector. The detector may detect the luminescence intensity of the complex and the luminescence intensity of the blood treated complex.

In other embodiments, the kit may further include a calculation unit which receives data of the luminescence intensity of the complex and the luminescence intensity of the blood treated complex from the detector and calculates a quenched degree of the luminescence intensity of the blood treated complex based on the luminescence intensity of the complex itself. The kit may further include a display capable of quantitatively or qualitatively displaying the quenched degree of the luminescence intensity.

Figure 11A:
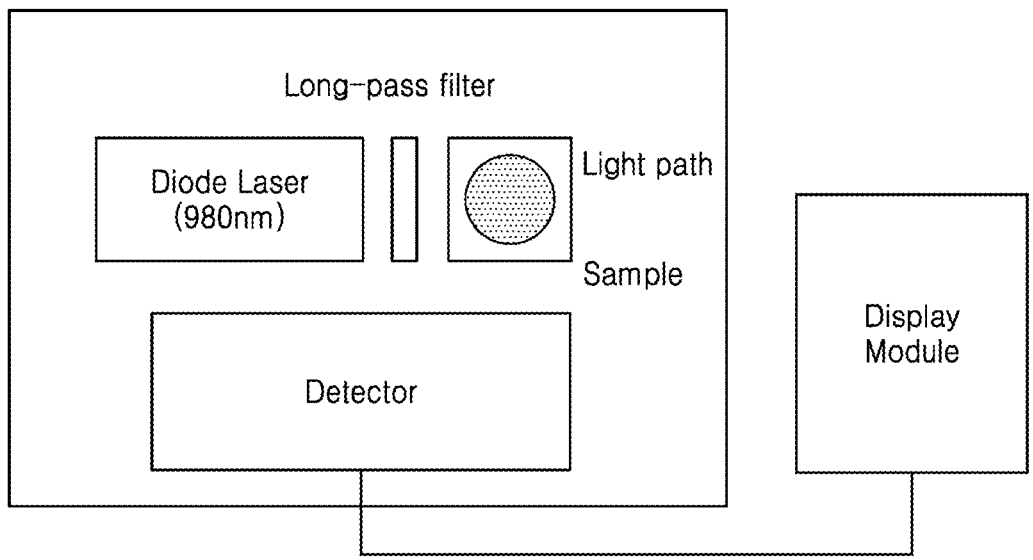
FIG. 11a and FIG. 11b show a plan view and a stereoscopic view of a diagnostic kit according to one embodiment of the present invention, respectively.
Figure 11B:
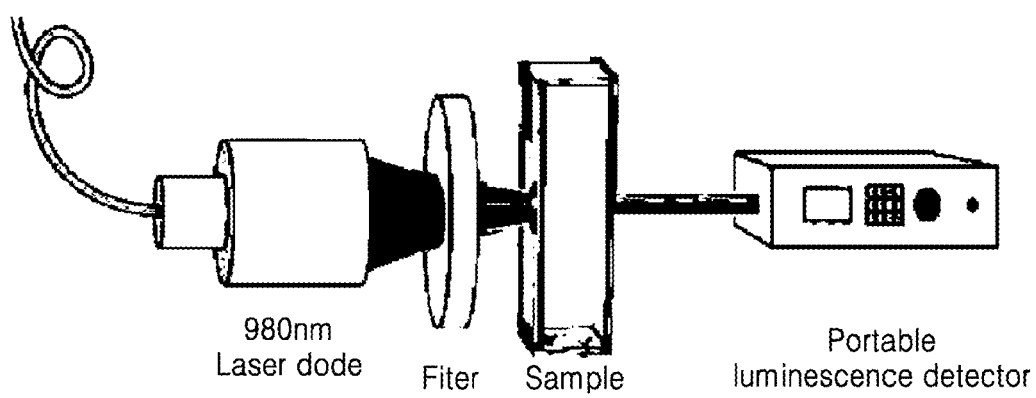

A plan view and a stereoscopic view of a diagnostic kit are shown in FIG. 11a and FIG. 11b, respectively.

Yet Another aspect of the present invention relates to a method for diagnosing diabetes, including: (A) bringing the blood taken from the human body into contact with a complex according to various embodiments of the present invention; and (B) exposing the complex brought into contact with blood to near-infrared light irradiation and measuring luminescence intensity.

Yet another aspect of the present invention relates to a method for preparing a complex including an antibody and upconverting nanoparticles covalently bound to the antibody.

The preparation method includes (A) coating upconverting nanoparticles with silica, (B) introducing an amine group to the silica-coated upconverting nanoparticles, (C) converting the amine group into a carboxylic group, and (D) binding the carboxylic group to an amine group of the enzyme.

According to one embodiment, step (A) is performed by reacting upconverting nanoparticles with tetraethoxy silane. Step (B) may be performed using aminopropyl trimethoxysilane. Step (C) may be performed using succinic anhydride. Step (D) may be performed by reacting 1-ethyl-3-(3-dimethylaminopropyl)carbodiimide (EDC) with hydroxysuccinimide (NHS).

Hereinafter, the present invention will be described in more detail with reference to some examples. It should be understood that these examples are provided for illustration only and are not to be construed in any way as limiting the present invention. The scope of the invention should be defined only by the accompanying claims and equivalents thereof.

The present invention provides a platform that detects glycated hemoglobin as an indicator for diabetes in the blood based on upconverting nanoparticles excited by near-infrared light and luminescence resonance energy transfer.

The upconverting nanoparticles absorb near-infrared light through sequential absorption of two or more photons, thereby emitting ultraviolet or visible light which has shorter wavelength than the excitation wavelength. Advantageously, the upconverting nanoparticles can regulate wavelength of signals emitted by regulating the types and concentrations of host, activators, or sensitizers while retaining luminescence of high signal intensity, good stability and biocompatibility.

Specifically, since near-infrared light is used in order to excite upconverting nanoparticles, the antibody or enzyme to be detected is protected from damage and problems such as quenching of the detected signals due to matrix effects induced by various by-products in the actual sample, and non-specific reactions are prevented.

In order to form the upconverting nanoparticles-antibody complex, the surface of the upconverting nanoparticles may be modified. Examples of methods for modifying the surface of the upconverting nanoparticles may include encapsulation of upconverting nanoparticles with polyethylene glycol, and silica coating of upconverting nanoparticles. The upconverting nanoparticles have an average diameter of about 40 nm to about 45 nm. The silica coating may have an average coating thickness of 8 nm to 10 nm. The upconverting nanoparticles with the coating thickness can respond to near-infrared light and be well dispersed in an aqueous solution, leading to binding to biomolecules.

As such, the upconverting nanoparticles-antibody complex is formed using the surface modified upconverting nanoparticles, thereby allowing various materials to be fixed to the upconverting nanoparticles without limitation. The receptor to be fixed may include at least one selected from the group comprising antibodies, enzymes, DNAs, aptamers, PNAs (peptide nucleic acids), and ligands.

The upconverting nanoparticles-antibody complex may be formed by physical or chemical bonds. Examples of chemical bonds may include covalent bonds, ionic bonds, and the like. Examples of physical bonds may include adsorption and the like.

The upconverting nanoparticles-antibody complex may serve as a donor. Materials having an absorbance similar to the wavelength of signals emitted under near-infrared light irradiation of the donor may serve as an acceptor. The specific antigen-antibody bonds between the antibody of the upconverting nanoparticles-antibody complex and a material to be detected allow luminescence resonance energy transfer from the donor to the acceptor. As the concentration of the acceptor as a material to be detected increases, the intensity of signals emitted from the upconverting nanoparticles gradually decreases. That is, the material to be detected can be quantitatively detected through quenched luminescence signals. Use of the upconverting nanoparticles having the luminescence signals overlapping with the absorbance wavelength of the material to be detected may allow effective detection of various materials to be detected by quenched luminescence signals via the luminescence resonance energy transfer due to a specific bond between the complex and the material to be detected.

Figure 1B:
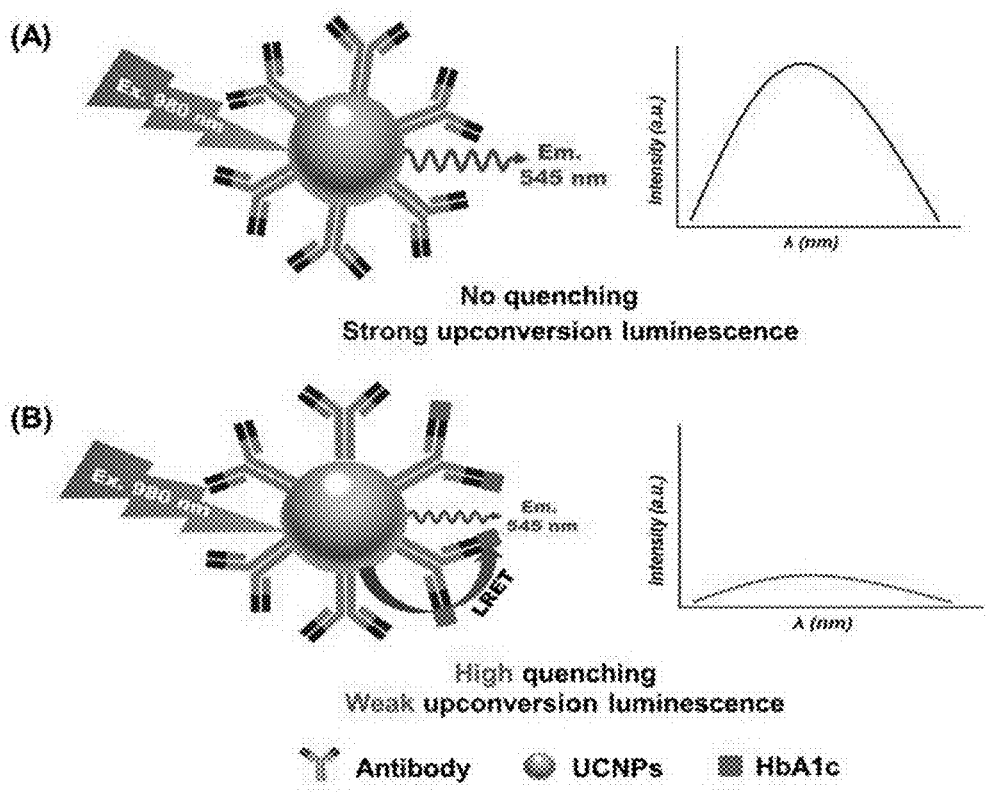
FIG. 1b shows a schematic view of luminescence resonance energy transfer from an upconverting nanoparticles-antibody complex donor to a glycated hemoglobin acceptor.

FIG. 1b shows a schematic view of luminescence resonance energy transfer from an upconverting nanoparticles-antibody complex donor to a glycated hemoglobin acceptor. When glycated hemoglobin as a material to be detected is present, the luminescence signal energy of the emitting upconverting nanoparticles-antibody complex is transferred to the glycated hemoglobin, thereby obtaining quenched luminescence signals.

The following description is given of the preparation of the upconverting nanoparticles-antibody complex by way of example.

Firstly, a mixed solution prepared by mixing a solvent with a precursor material of upconverting nanoparticles is subjected to heat treatment, followed by cooling the resulting solution to room temperature, and adding methanol containing sodium hydroxide and ammonium fluoride to the resulting solution. Next, the resulting solution is heat treated under nitrogen gas for 1 hour, followed by cooling to room temperature, and precipitating and washing with ethanol to obtain upconverting nanoparticles.

The upconverting nanoparticles subjected to surface modification with the silica coating are dispersed together with a surfactant (Igepal CO-520) and ammonia using an ultrasonicator. To this end, tetraethoxysilane (tetraethylorthosilicate) as a silica precursor is added dropwise at room temperature for 6 hours, precipitated with acetone, followed by washing with ethanol twice. Subsequently, 2% aminopropyltrimethoxysilane (APTMS) is added in order to introduce an amine group to the silica-coated upconverting nanoparticles. Finally, succinic anhydride is added to replace the amine group with a carboxylic group.

The carboxylic group of the carboxylated upconverting nanoparticles and an amine group of the antibody may form amide bonds. In order for EDC/NHS reaction of 1-ethyl-3-(3-dimethylaminopropyl)carbodiimide (EDC) and N-hydroxysuccinimide (NHS) to be used in formation of an amide bond, for example, 1-ethyl-3-(3-dimethylaminopropyl)carbodiimide (EDC) and N-hydroxysuccinimide (NHS) are added to the modified carboxylated silica-coated upconverting nanoparticles.

The present invention will be further described with reference to the following examples which should not be construed as limiting the present invention. Further, it will become apparent to those skilled in the art that the present invention can be easily practiced based on the disclosure of the present invention including the following examples. Naturally, any variants and modifications fall within the scope of the attached claims.

EXAMPLES

Experimental Example 1: Confirmation of Properties of Synthesized Upconverting Nanoparticles To a mixed solution consisting of 8 mL of oleic acid and 15 mL of octadecene, 0.78 mmol $YCl_3$ (Yttrium (III) chloride), 0.2 mmol $YbCl_3$ (Ytterbium (III) chloride), and 0.02 mmol $ErCl_3$ (Erbium (III) chloride) were added, followed by heat treatment up to 160° C. while stirring the mixed solution under nitrogen gas. Then, the resulting solution was maintained in a vacuum for 30 minutes and cooled to room temperature. Then, methanol comprising 0.25 M sodium hydroxide and 0.4 M ammonium fluoride was added to the resulting solution. The resulting solution was heat treated up to 300° C. under nitrogen gas, maintained for 1 hour, cooled to room temperature, followed by precipitating and washing with ethanol, thereby obtaining upconverting nanoparticles.

Figure 2:
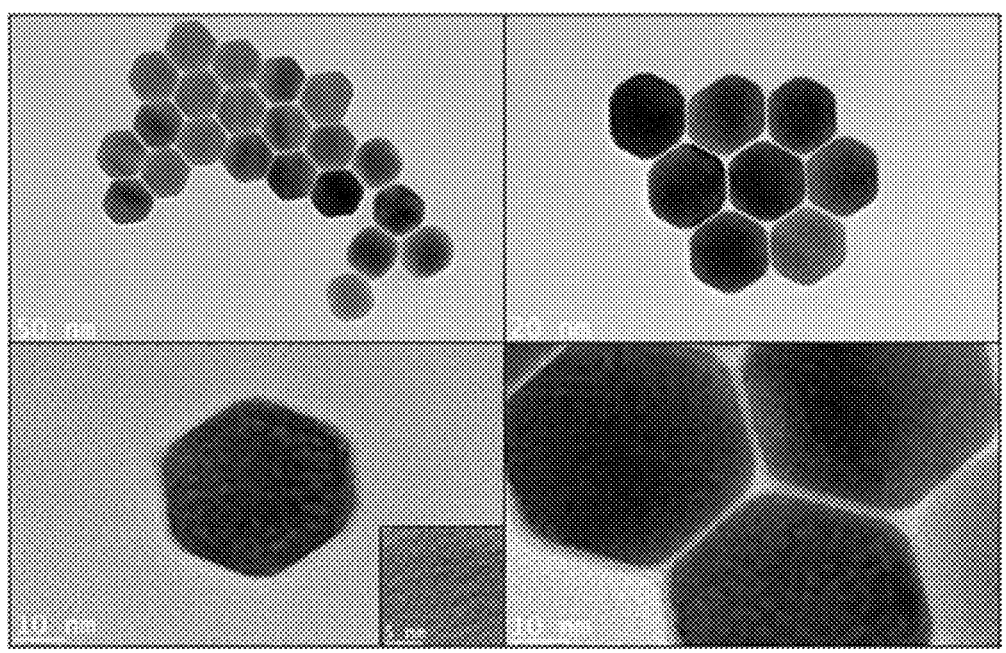
FIG. 2 shows a transmission electron microscope (TEM) image of upconverting nanoparticles synthesized in Examples.

The shape and size of the synthesized upconverting nanoparticles were measured by transmission electron microscopy. FIG. 2 shows a transmission electron microscope (TEM) image of the synthesized upconverting nanoparticles. The nanoparticles have a hexagonal lattice structure and an average diameter of about 40 nm to about 45 nm.

Figure 3:
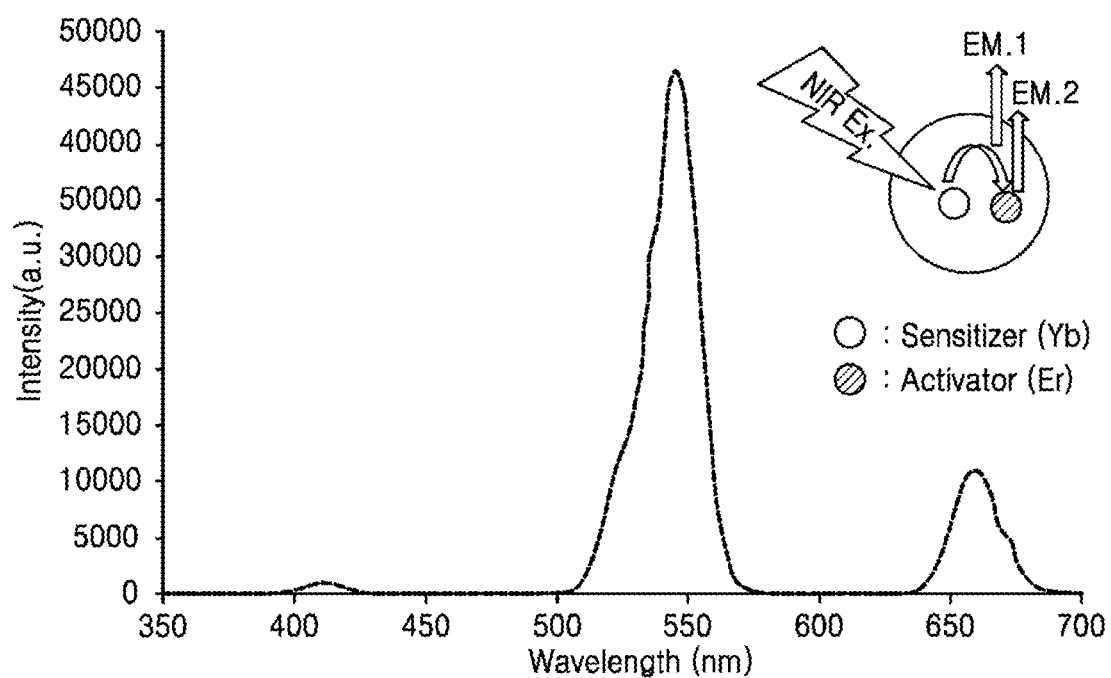
FIG. 3 shows a spectrum result and an image of light emitted from upconverting nanoparticles synthesized in Examples after exposure to a laser diode emitting near-infrared light having a wavelength of 980 nm.

FIG. 3 shows a spectrum result and a signal image of green light emitted from the synthesized upconverting nanoparticles after exposure to a laser diode emitting near-infrared light having a wavelength of 980 nm, wherein the spectrum has major peaks at 540 to 550 nm (green light) and 650 to 670 nm (red light) as measured by a fluorescence and luminescence spectrometer (model name: FS-2, manufactured by Shinco Inc. (Korea)).

Figure 4A:
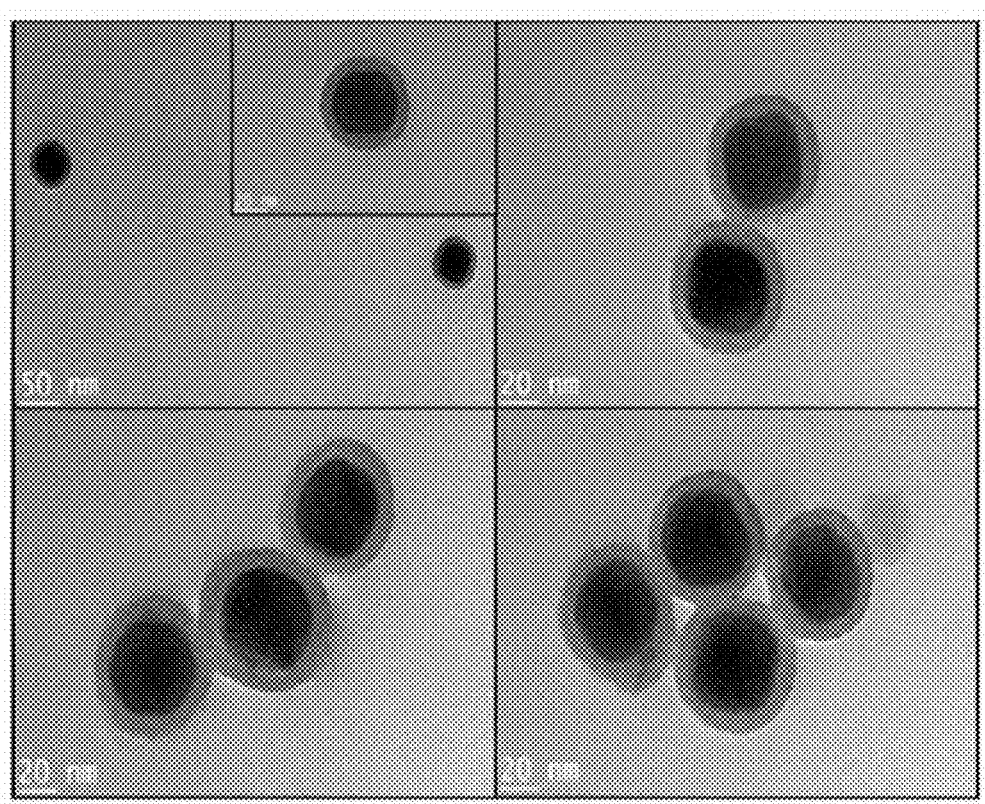
FIG. 4a shows a transmission electron microscope (TEM) image of upconverting nanoparticles, surfaces of which are modified with carboxylic groups in order to bind a specific antibody for glycated hemoglobin to upconverting nanoparticles synthesized in Examples.

Experimental Example 2: Confirmation of Properties of Silica-Coated Upconverting Nanoparticles The size and surface potential of silica-coated upconverting nanoparticles subjected to surface modification with a carboxylic group were measured using a transmission electron microscope and zeta-potential analyzer. It was confirmed that the silica-coated upconverting nanoparticles subjected to surface modification with a carboxylic group had a coating thickness of about 8 nm to about 10 nm via transmission electron microscope images shown in FIG. 4a.

Figure 4B:
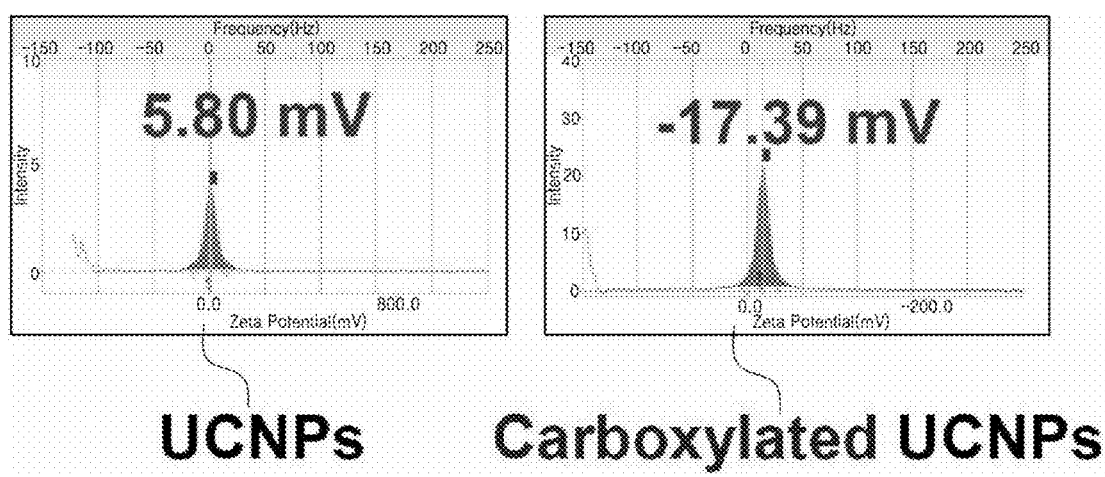
FIG. 4b shows zeta-potential analysis results of upconverting nanoparticles, surfaces of which are modified with carboxylic groups.

As shown in FIG. 4b, the surface potential of the upconverting nanoparticles was determined by a Zeta-potential analyzer [Model name: ELS Z, manufactured by Photal Otsuka electronics (Japan)]. From the result, it was confirmed that the surface of the upconverting nanoparticles was negatively charged due to surface modified carboxylic groups from 5.80 mV (before surface modification) to −17.39 mV (after modification using carboxylic groups).

Figure 5:
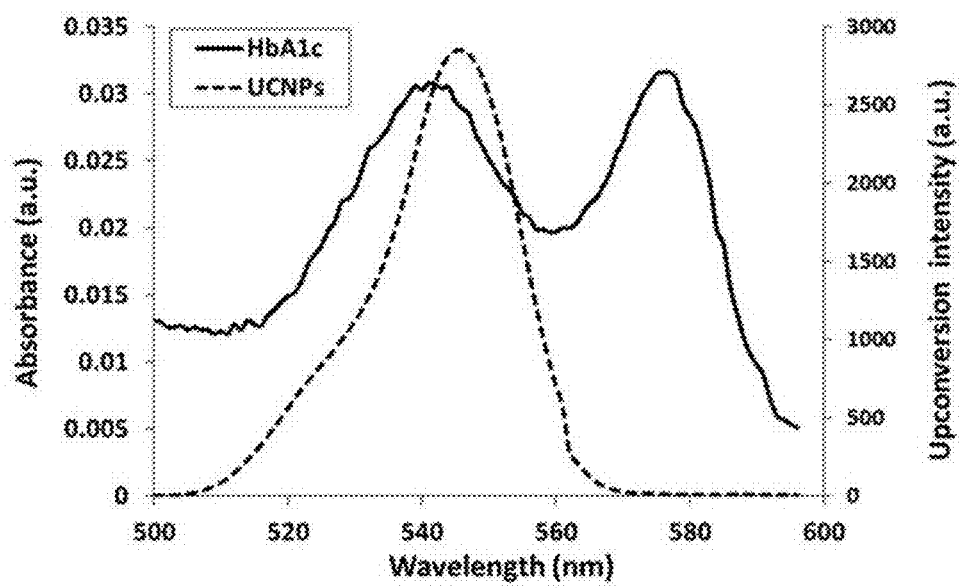
FIG. 5 shows a spectrum of light emitted from upconverting nanoparticles-antibody complexes synthesized in Examples after exposure to a laser diode emitting near-infrared light having a wavelength of 980 nm and an absorbance spectrum of glycated hemoglobin.

Experimental Example 3: Confirmation of Luminescence Resonance Energy Transfer Between Upconverting Nanoparticles-Antibody Complex and Glycated Hemoglobin FIG. 5 shows a spectrum of light emitted from the synthesized upconverting nanoparticles-antibody complex after exposure to a laser diode emitting near-infrared light having a wavelength of 980 nm and an absorbance spectrum of glycated hemoglobin. It was confirmed that signals around 500 nm to 560 nm emitted from the upconverting nanoparticles-antibody complex considerably overlapped the absorbance signals of glycated hemoglobin to be detected. This result suggests that there was a possibility of luminescence resonance energy transfer from an upconverting nanoparticles-antibody complex donor to a glycated hemoglobin acceptor due to a specific bond between an antibody and glycated hemoglobin to be detected.

Figure 6:
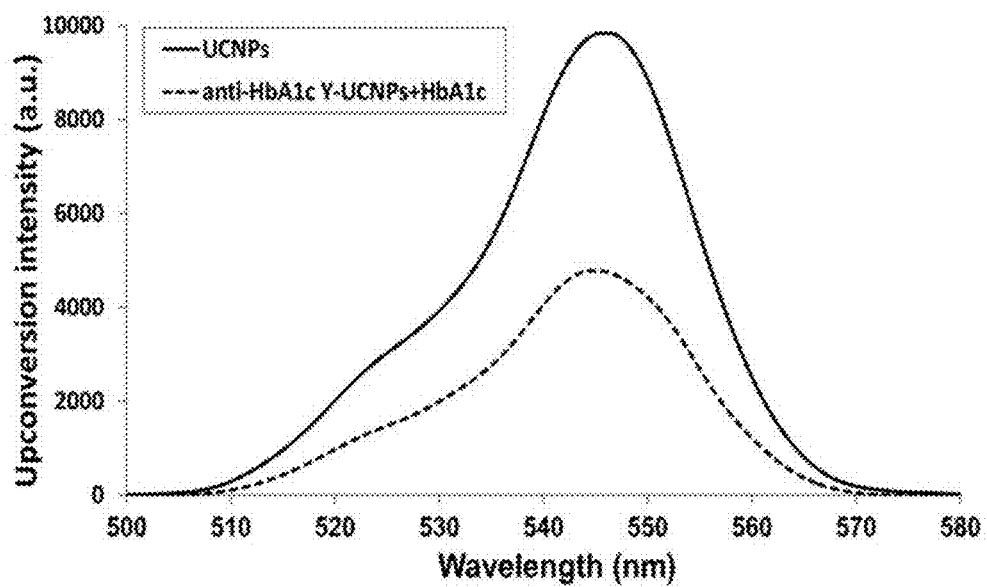
FIG. 6 shows a spectrum of quenched luminescence signals by luminescence resonance energy transfer of upconverting nanoparticles-antibody complexes synthesized in Examples in the presence of glycated hemoglobin.

FIG. 6 shows a spectrum of quenched luminescence signals of the upconverting nanoparticles-antibody complex in the presence of glycated hemoglobin. Upon adding 17% to 22% glycated hemoglobin, about 50% quenched luminescence signals were obtained after reaction with the upconverting nanoparticles-antibody complex. From this result, it was confirmed that an effective luminescence resonance energy transfer occurred from the upconverting nanoparticles-antibody complex donor to the glycated hemoglobin acceptor.

Figure 7:
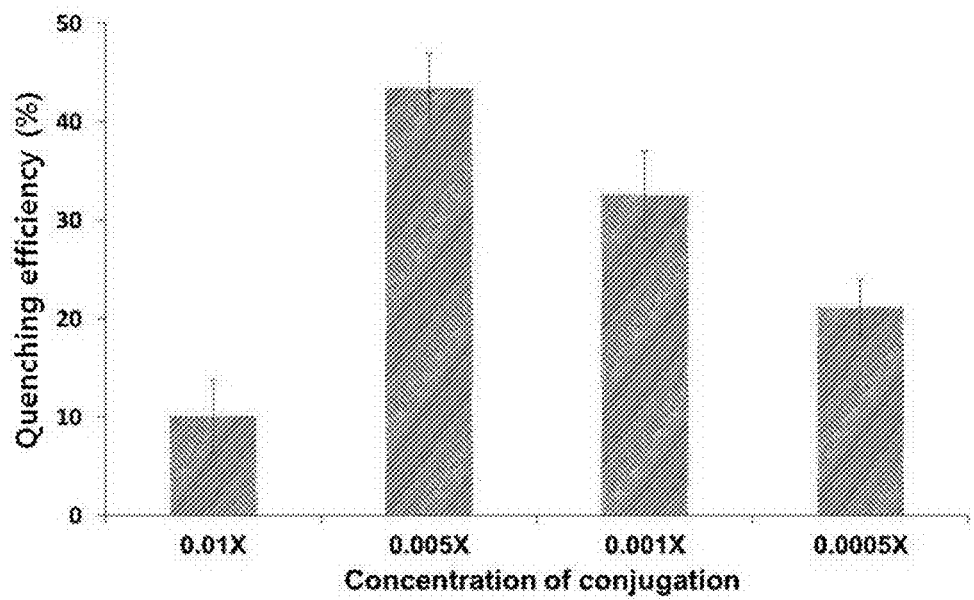
FIG. 7 shows a graph depicting quenching efficiency of luminescence signals of upconverting nanoparticles-antibody complexes in various concentrations synthesized in Examples in the presence or absence of glycated hemoglobin.

FIG. 7 shows a graph depicting quenching efficiency of luminescence signals of the synthesized upconverting nanoparticles-antibody complex in various concentrations in the presence or absence of glycated hemoglobin. It was confirmed that the largest quenching efficiency was observed when the synthesized complex was diluted to 0.005×.

Figure 8:
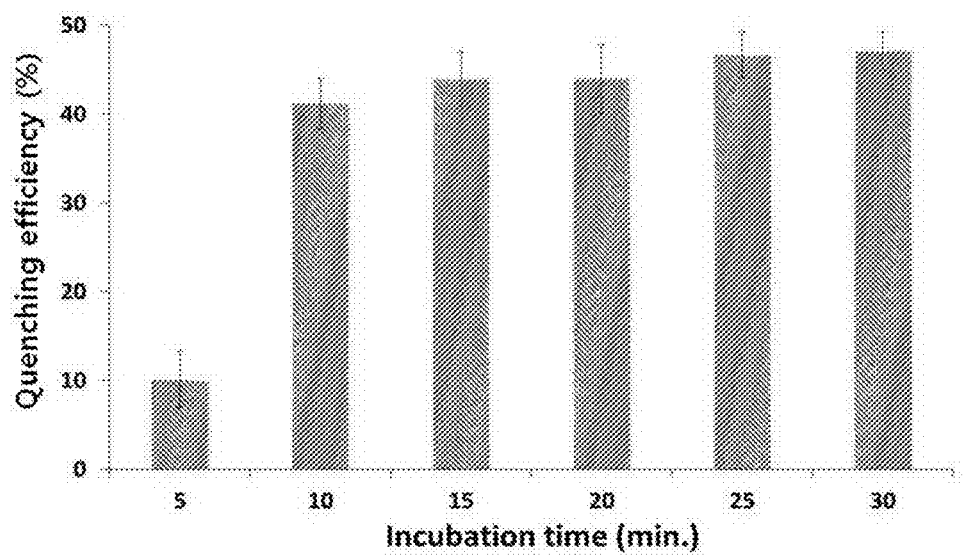
FIG. 8 shows a graph depicting quenching efficiency of luminescence signals of upconverting nanoparticles-antibody complexes synthesized in Examples over various incubation times with glycated hemoglobin in the presence or absence of glycated hemoglobin.

FIG. 8 shows a graph depicting quenching efficiency of luminescence signals of the upconverting nanoparticles-antibody complexes synthesized in Examples over various incubation times with glycated hemoglobin in the presence or absence of glycated hemoglobin. It was confirmed that if reaction was performed for 10 minutes or more, effective luminescence resonance energy transfer occurred due to a specific bond between the antibody and glycated hemoglobin to be detected.

Figure 9:
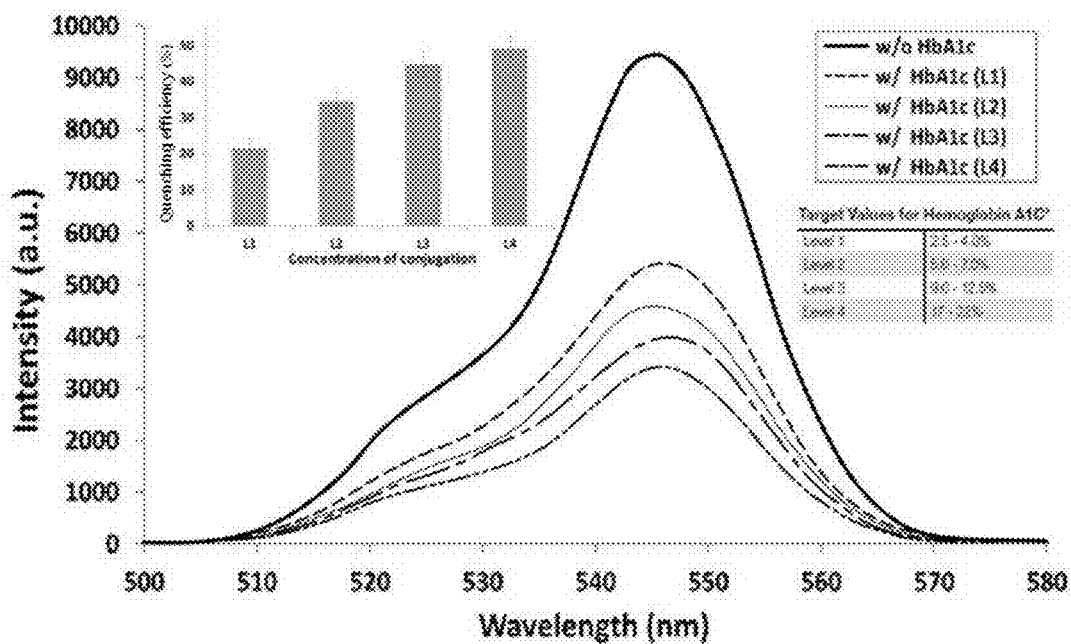
FIG. 9 shows a spectrum of quenching luminescence signals and quenching efficiency depending upon standard samples containing various concentrations of glycated hemoglobin under the optimized conditions in Examples.

Experimental Example 4: Detection of Glycated Hemoglobin by Luminescence Resonance Energy Transfer in Blood Sample FIG. 9 show a spectrum of quenching luminescence signals and quenching efficiency depending upon standard samples (Lyphochek® Hemoglobin A1C Linearity Set, manufactured by Biorad) containing various concentrations of glycated hemoglobin under the optimized conditions in Example (0.005× diluted upconverting nanoparticles-antibody complex and 10 minutes reaction time). It was confirmed that the intensity of signals emitted from the upconverting nanoparticles-antibody complex gradually decreased depending upon the concentration of acceptor to be detected. Four different samples according to glycated hemoglobin levels (levels 1 to 4) exhibited quenching efficiency from about 21% to about 49%.

Figure 10:
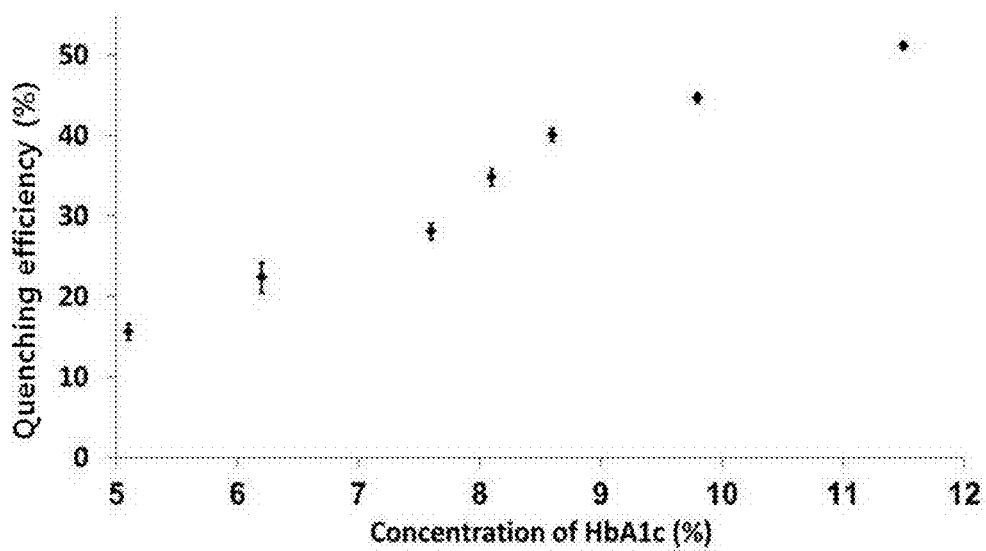
FIG. 10 shows a graph depicting quenching efficiency of luminescence signals depending upon actual samples containing various concentrations of glycated hemoglobin under the optimized conditions in Examples.

FIG. 10 shows a graph depicting quenching efficiency of luminescence signals depending upon actual samples containing various concentrations of glycated hemoglobin under the optimized conditions in Example. It was confirmed that quenching efficiency of the actual blood samples containing various content of glycated hemoglobin ranging from 5.1% to 11.5% revealed gradual decrease with increasing concentration of glycated hemoglobin.

From the above results, it can be seen that luminescence resonance energy transfer from the upconverting nanoparticles-antibody complex donor to the glycated hemoglobin acceptor is facilitated as the concentration of glycated hemoglobin in the blood increases, which in return allows the glycated hemoglobin to absorb the luminescence signals of the upconverting nanoparticles-antibody complex, thereby increasing quenching efficiency of the luminescence signals.

Although some embodiments have been described herein, it should be understood by those skilled in the art that these embodiments are given by way of illustration only, and that various modifications, variations, and alterations can be made without departing from the spirit and scope of the invention. Therefore, the scope of the invention should be limited only by the accompanying claims and equivalents thereof.

What is claimed is:

1. A complex for detecting glycated hemoglobin, comprising:
   (i) a specific receptor for glycated hemoglobin; and
   (ii) upconverting nanoparticles bound to the specific receptor,
   wherein the specific receptor for glycated hemoglobin is an antibody that is a material capable of specifically binding to the glycated hemoglobin,
   wherein the upconverting nanoparticles comprise rare earth elements and is free from additional metal nanoparticles,
   wherein the upconverting nanoparticles and the antibody are bound by an amide bond which is formed between a carboxylic group introduced to surfaces of the upconverting nanoparticles and an amine group of the antibody.

2. The complex according to claim 1, wherein the antibody is an anti-HbA1c monoclonal antibody.

3. The complex according to claim 1, wherein the bond is formed by reacting 1-ethyl-3-(3-dimethylaminopropyl)carbodiimide (EDC) with hydroxysuccinimide (NHS).

4. The complex according to claim 1, wherein the upconverting nanoparticles are subjected to surface modification by polyethylene glycol (PEG) encapsulation or silica coating.

5. The complex according to claim 1, wherein the upconverting nanoparticles have an average particle diameter of 40 nm to 45 nm and the silica coating has an average thickness of 8 nm to 10 nm.

6. A kit for diagnosing diabetes comprising the complex of claim 1.

7. The kit according to claim 6, wherein the upconverting nanoparticles are subjected to surface modification by polyethylene glycol (PEG) encapsulation or silica coating.

8. The kit according to claim 6, further comprising: a near-infrared light source.

9. The kit according to claim 8, further comprising: a detector.

* * * * *